(12) United States Patent
Gundry

(10) Patent No.: US 6,524,338 B1
(45) Date of Patent: Feb. 25, 2003

(54) METHOD AND APPARATUS FOR STAPLING AN ANNULOPLASTY BAND IN-SITU

(76) Inventor: Steven R. Gundry, 7 Bow C Rd., Redlands, CA (US) 92373

(*) Notice: Subject to any disclaimer, the term of this patent is extended or adjusted under 35 U.S.C. 154(b) by 37 days.

(21) Appl. No.: 09/648,574

(22) Filed: Aug. 25, 2000

(51) Int. Cl.$^7$ .................................................. A61F 2/06

(52) U.S. Cl. ...................................... 623/2.11; 623/2.36

(58) Field of Search .............................. 623/2.11, 2.36, 623/2.37, 2.41, 904; 606/99, 140, 151

(56) References Cited

U.S. PATENT DOCUMENTS

| | | | |
|---|---|---|---|
| 3,656,185 A | | 4/1972 | Carpentier ........................... 3/1 |
| 4,042,979 A | | 8/1977 | Angell ............................. 3/1.5 |
| 4,055,861 A | | 11/1977 | Carpentier ....................... 3/1.5 |
| 4,144,046 A | | 3/1979 | Esposito ......................... 71/86 |
| 4,164,046 A | * | 8/1979 | Cooley ........................... 3/1.5 |
| 4,602,911 A | * | 7/1986 | Ahmadi et al. .................. 623/2 |
| 5,011,481 A | * | 4/1991 | Myers et al. .................... 606/1 |
| 5,290,300 A | | 3/1994 | Cosgrove et al. ........... 606/148 |
| 5,522,884 A | * | 6/1996 | Wright ............................ 623/2 |
| 5,669,919 A | * | 9/1997 | Sanders et al. ............. 606/148 |
| 5,716,370 A | | 2/1998 | Williamson, IV et al. .. 606/153 |
| 5,843,177 A | * | 12/1998 | Vanney et al. .................. 623/2 |
| 5,972,004 A | | 10/1999 | Williamson, IV et al. .. 606/142 |
| 6,102,945 A | * | 8/2000 | Campbell .................... 623/2.37 |
| 6,106,550 A | | 8/2000 | Magovern et al. ......... 623/2.38 |
| 6,197,054 B1 | | 3/2001 | Hamblin et al. ............ 623/2.38 |
| 6,241,765 B1 | | 6/2001 | Griffin et al. ............... 623/2.38 |
| 6,287,339 B1 | | 9/2001 | Vazquez et al. ............. 623/2.4 |

FOREIGN PATENT DOCUMENTS

| | | |
|---|---|---|
| WO | 99/29269 | 6/1999 |
| WO | 99/53845 | 10/1999 |

OTHER PUBLICATIONS

Carpentier,A., Delocke,A., Dauptain J., Soyer, R., Blondeau, P., Piwnica, A., Dubost, Ch., and McGoon, D.: A new reconstructive operation for correction of mitral and tricuspid insufficiency,J. Thorac. Cardiovasc.Surg. 61: 1, 1971.

Murphy,P., Sweeney,M., and Cooley, D.: The Puig–Massana–Shiley Annuloplasty Ring for Mitral Valve Repair: Experience in 126 Patients, Ann. Thorac. Surg. 43:52–58, 1987.

Gorton, M., Piehler, J., Killen, D., Hoskins, M., and Borkon, M.: Mitral Valve Repair Using a Flexible and Adjustable Annuloplasty Ring: Ann Thorac.Surg. 55:860–863, 1993.

Johannesson, Th., Ahmadi, A., and Spillner, G., : HemodynamicChanges Following Experimental Production and Correction of Acute Mitral Regurgitation with an Adjustable Ring Prosthesis, Thorac. Cardiovasc. Surgeon 36: 313–319, 1988.

Alonso–Lej, F.: Adjustable Annuloplasty for Tricuspid Insufficiency with External Control, The Am. Journal of Card 73; 721–722, 1994.

Carpentier, A., Lessana, A., Relland, J., Belli, E., Mihaileanu, S., Berrebi, A., Palsky, E., and Loulmet, D.: The "Physio–Ring": An Advanced Concept in Mitral Valve Annuloplasty, Ann. Thorac. Surg. 60: 1177–1186, 1995.

Cosgrove, D., Arcidi, J., Rodriguez, L., Stewart, W., Powell, K., and Thomas, J.: Initial Experience With the Cosgrove–Edwards Annuloplasty System, Ann.Thorac. Surg. 60: 499–504, 1995.

* cited by examiner

*Primary Examiner*—Bruce Snow

(57) ABSTRACT

Apparatus and method for stapling a prosthesis in-situ includes an adjustable annuloplasty band and a positioning instrument for holding and positioning the band in a heart valve annulus. The instrument includes a curvature adjustable portion at one end for adjusting the band to conform to the heart valve annulus. Another end of the instrument, opposite the one end, includes a curvature adjustment actuating means. A stapling device attaches the band to the annulus simultaneously with the band being held in the annulus by the positioning instrument.

10 Claims, 5 Drawing Sheets

METHOD AND APPARATUS FOR STAPLING AN ANNULOPLASTY BAND IN-SITU

BACKGROUND

The disclosures herein related generally to a prosthesis and more particularly to an apparatus and method for stapling an annuloplasty band in-situ.

A conventional ring, disclosed in U.S. Pat. No. 4,055,861, completely surrounds the mitral or tricuspid valve annulus with the intent of supporting the entire annulus to prevent dilatation of the natural tissue. U.S. Pat. No. 4,144,046 discloses an early use of a flexible, partial ring or band. Subsequently, U.S. Pat. No. 4,164,046 disclosed a partial ring or band that reinforces the posterior portion of the mitral valve annulus but does not extend across the anterior portion of the annulus. It was believed by many that the fibrous anterior portion of the annulus is not subject to dilatation, in contrast to the muscular posterior portion of the annulus. Operative time can be reduced with the implantation of a partial band because fewer sutures are required to secure the band to the native valve annular tissue. Further, there is some risk of damaging the aortic valve leaflets when placing sutures in the anterior portion of the mitral valve annulus. A partial band limits this concern. Some surgeons do not use partial bands because in some cases, patients have experienced dilation of the fibrous anterior tissue. As a result, many surgeons continue to employ a complete ring.

Complete rings can be constructed at the operating table by the surgeon or purchased as a preconstructed product under the name Medtronic/Duran(tm) Annuloplasty Ring. Still, in many cases anterior reinforcement is not required, and therefore partial bands are used in some patients. Partial bands can be constructed at the operating table and are also commercially available under the name Baxter/Cosgrove (tm) Annuloplasty Ring.

There are several other known annuloplasty ring devices. U.S. Pat. No. 3,656,185 discloses a cardiac valvular prosthesis, e.g., for the mitral valve, consisting solely of an annular or part-annular member adapted to fit against the base of the cusps of a human heart valve and suture means for securing the member in place. The prosthesis cooperates with the natural valve cusps of the patient to form the valve. This device is a semi-rigid band with a shape that matches the correct anatomical shape of the native valve, allowing remodeling of the valve.

U.S. Pat. No. 4,042,979 discloses an adjustable valvuloplasty ring that comprises a C-shaped frame that is sized and shaped to extend about the circumference of the left atrio-ventricular orifice along the base of the anterior cusp of the mitral valve; an expandable sleeve connected to the frame that together therewith forms a closed annulus, the sleeve being adapted to extend about the remainder of the circumference of the orifice; and a drawstring running through the sleeve by which the sleeve may be contracted to constrict and remodel the orifice and secured in place to maintain such constriction. This ring is entirely flexible.

U.S. Pat. No. 4,164,046 discloses a valve prosthesis for mitral and tricuspid heart valves. The prosthesis is configured as an open band covered with a double velour fabric having a laterally projecting fabric appendage for simultaneously facilitating suturing the prosthesis in place and improving tissue infiltration.

U.S. Pat. No. 5,290,300 discloses an assembly for holding a substantially flexible suture guide of predetermined length in a substantially taut position used to achieve a suture line having a dimension equal to the length of the suture guide, such as the circumference about a heart valve annulus. The assembly includes a rigid suture guide holder having a surface against which the length of suture guide is releasably positioned. The guide holder can have a shape or geometry, such as a circumference or circumferential segment, equivalent to the shape or geometry of the intended suture line. The shape of the guide holder can therefore be selected to hold the suture guide in the shape most advantageous to placing the desired suture line. The assembly further includes a mechanism for releasably binding the suture guide to the surface of the holder and a detachable handle extendibly attached to the holder by means of a lanyard so that the handle can be detached to afford an unobstructed view of the surgical site, but cannot be removed from the surgical site until the holder has also been removed.

U.S. Pat. No. 5,716,370 discloses a heart valve is which can be replaced using minimally invasive methods which include a sutureless sewing cuff and a fastener delivery tool that holds the cuff against the patient's tissue while delivering fasteners, two at a time in opposite directions, to attach the cuff to the tissue from the inside out. Drawstrings are operated from outside the patient's body and cinch the sewing cuff to the valve body. The cuff is releasably mounted on the tool. The tool stores a plurality of fasteners thereon. Two rows of staggered fasteners are formed whereby fasteners are located continuously through-out the entire circumference of the cuff. A minimally invasive surgical method is disclosed, and a method and tool are disclosed for repairing abdominal aortic aneurysms in the minimally invasive manner.

The diagnosis of mitral and tricuspid regurgitation has been greatly simplified by advances in echocardiography. Initial diagnosis is possible with simple transthoracic echocardiography (TTE) that carries no risk for the patient. Detailed examination of the pathology is possible with transesophageal echocardiography that carries an extremely low risk for the patient. Despite the advances in diagnostic technology, current practice delays treatment of mitral and tricuspid valve pathology because the surgical morbidity creates risks that the patient and surgeon are reluctant to bear before the disease causes noticeable symptoms. By the time symptoms become noticeable, structural degradation of the valve is likely to have taken place, which might have been prevented by early intervention. This structural degradation of the valve often requires complex surgical maneuvers to correct the pathology or even replacement of the entire valve.

Therefore, what is needed is an apparatus and a method for reducing time and trauma associated with mitral valve repair.

SUMMARY

One embodiment, accordingly, reduces time and trauma associated with mitral valve repair by replacing sutures with staples which are quickly applied through smaller, less traumatic incisions. To this end, apparatus is provided for attaching a prosthesis in-situ including an annuloplasty band, a positioning instrument for holding and positioning the band in a heart valve annulus, and a stapling device for attaching the band to the annulus simultaneously with the band being held in the annulus by the positioning instrument.

A principal advantage of this embodiment is that it reduces the time and trauma associated with mitral valve repair by replacing sutures with staples that can be applied more quickly by inserting the positioning instrument through a first small incision and by inserting the stapling device through a second small incision. Also, this embodiment allows more rapid placement of an annuloplasty band so that the time for patient exposure to cardiopulmonary bypass is substantially reduced.

DETAILED DESCRIPTION

Figure 1:
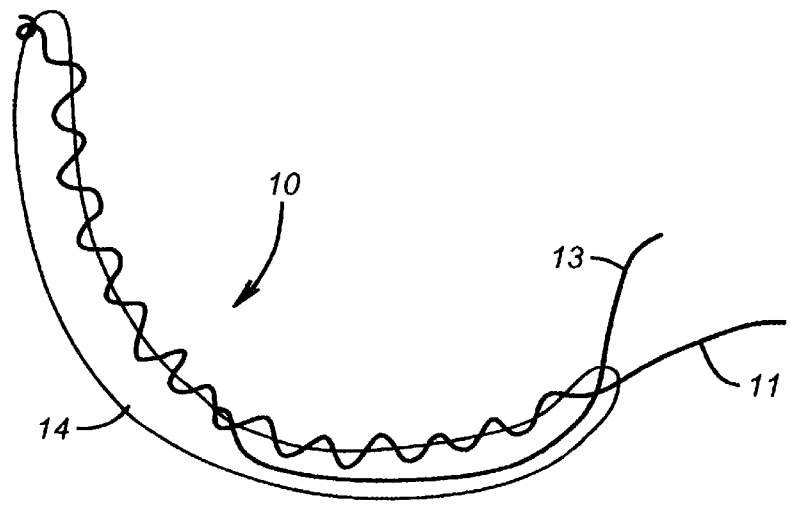
FIG. 1 is a perspective view illustrating an embodiment of an annuloplasty repair device.
Figure 2:
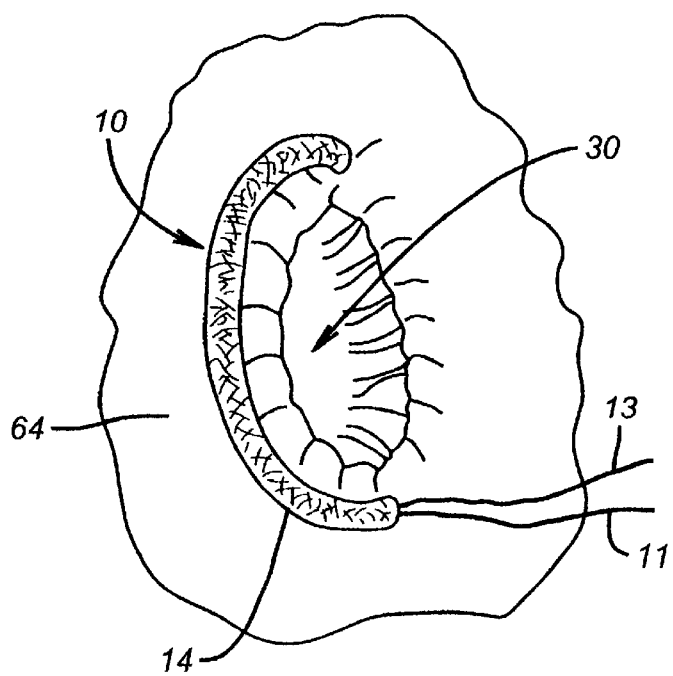
FIG. 2 is a perspective view illustrating the annuloplasty device of FIG. 1 reinforcing a portion of a heart valve.

An annuloplasty repair device, FIGS. 1 and 2, is generally designated 10 and includes an adjustable band 14. The adjustable band 14 is generally "C" shaped to fit over the posterior valve annulus 64 of a mitral valve 30. Band 14 includes a left adjusting suture 13 and a right adjusting suture 11. Sutures 13 and 11 exit band 14 at a point where the sutures 13 and 11 can pass through a wall of a human heart at a location where an incision is made for a positioning instrument (discussed below). Such bands 14 are often used as a support for the human heart valve such as a mitral valve, or sometimes used for tricuspid valve support. As such, band 14 comprises a cardiac valvular prosthesis for a heart valve. As a result, the surgeon may use a band 14 to reinforce the mitral valve 30, FIG. 2.

Figure 3:
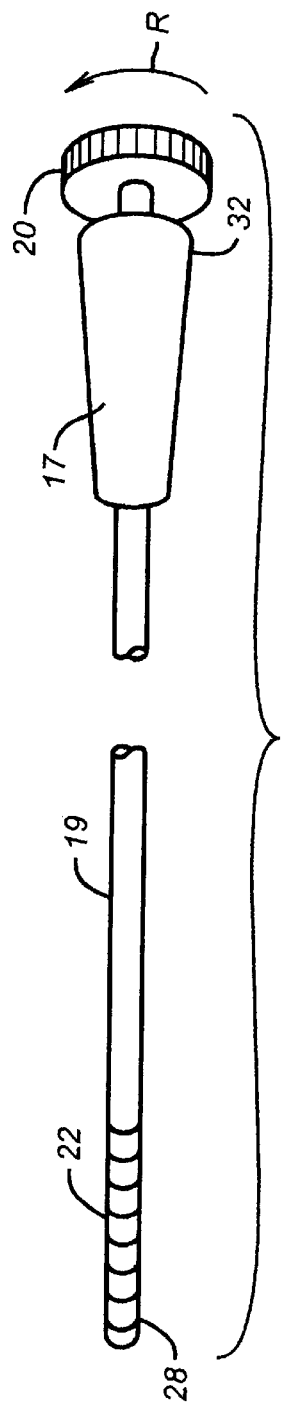
FIG. 3 is a view illustrating an embodiment of a positioning instrument.
Figure 4:
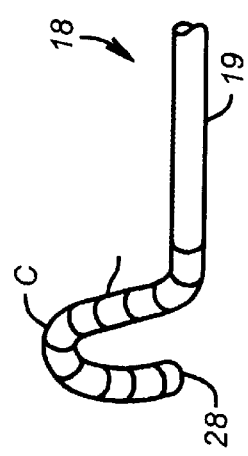
FIG. 4 is a view illustrating an adjustable portion of the position instrument of FIG. 3.
Figure 5:
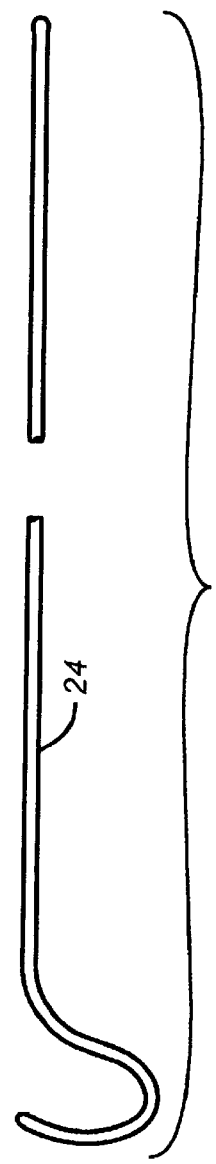
FIG. 5 is a view illustrating an embodiment of another positioning instrument.

The present disclosure is for the posterior band 14 to be attached to a flexible positioning instrument, discussed below, intended to hold the band 14 at a specific location adjacent to the annular tissue for attachment with staples to a mitral valve annulus or a tricuspid valve annulus. A positioning instrument 18, FIG. 3, is commercially available, such as the product sold under the name Genzyme EndoFlex(r). Instrument 18 includes a grip portion 17 having a movable handle 20 at an end 32 for rotation in the direction indicated by an arrow R. A curvature adjustable portion 22 of instrument 18 is at another end 28. A stem 19 interconnects first and second opposite ends 32, 28, respectively. Movable handle 20 is rotatable for changing a curvature designated C of portion 22 of the instrument 18, FIG. 4, by placing tension on an internal wire (not shown) running down the center of the stem 19 of instrument 18. A simple fixed shape curved rod 24, FIG. 5, could also be used to position the band 14 in place for stapling, but the flexible positioning instrument 18 is preferred. The handle 20 functions as a curvature adjustment actuating means.

Figure 6:
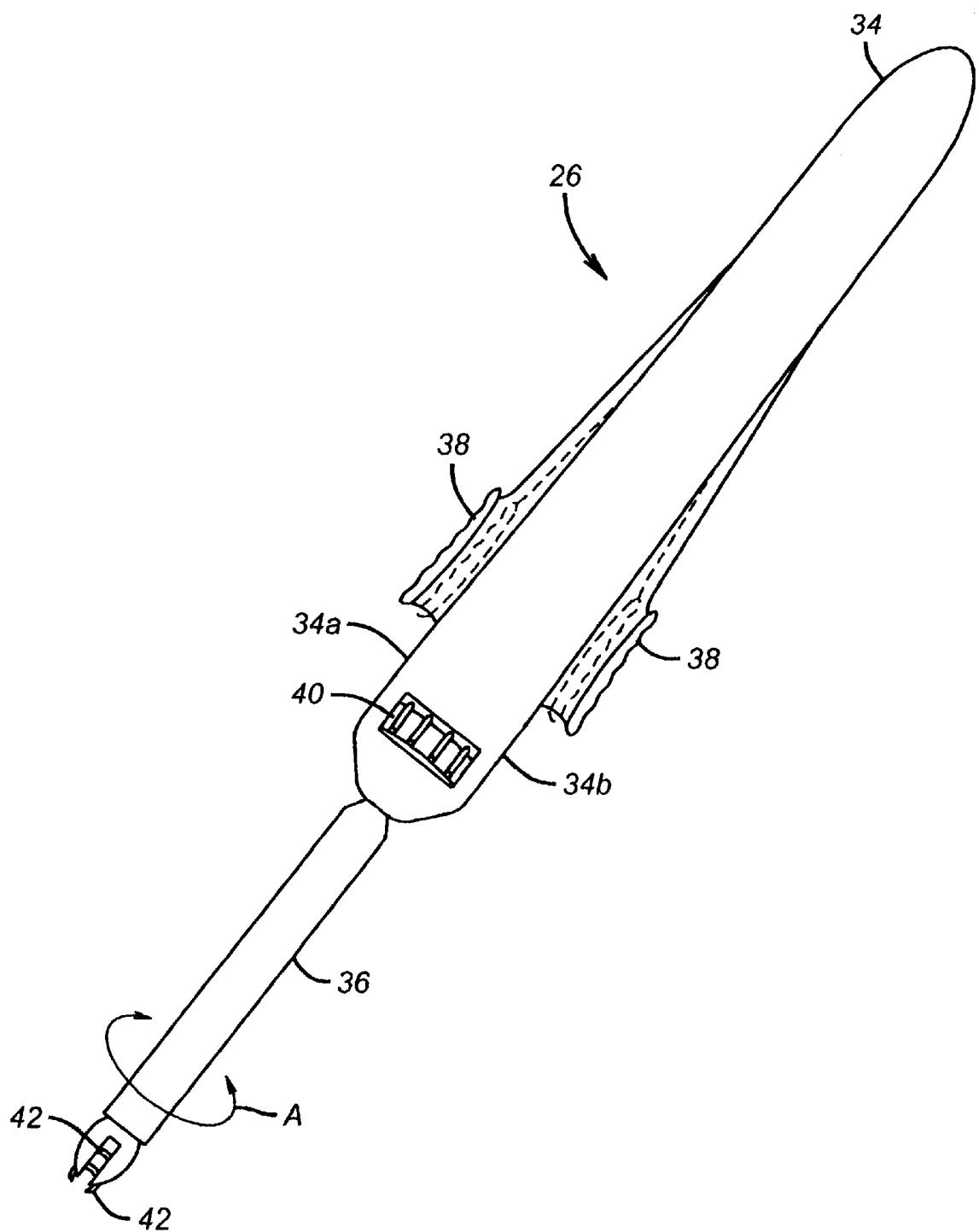
FIG. 6 is a view illustrating an embodiment of a clip applier or surgical stapling instrument.

A commercially available clip applier or stapling device 26, FIG. 6, such as the product sold under the name Auto Suture VCS, includes a handle portion 34 and a staple delivery portion 36. Handle portion 34 is elongated and includes a pair of movable members 38 which are mounted on opposite sides 34a, 34b of handle portion 34, and can be depressed into the handle portion 34, as illustrated in phantom, for actuating the staple delivery portion 36. Staple delivery portion 36 stores open staples or clips 42 for sequential delivery. Portion 36 is elongated and rotatably extends from handle portion 34 for unlimited clockwise and counterclockwise rotation as indicated by the bidirectional arrow designated A. Rotation is manually accomplished by rotating a star wheel 40 mounted in handle portion 34 and connected to staple delivery portion 36. When the staple delivery portion 36 is positioned at a desired site, and rotated the desired amount, the movable members 38 may be manually depressed by pinching them inwardly toward the handle portion 34. As a result, staples or clips 42 stored in the staple delivery portion 36 are closed (i.e. deformed) for attaching band 14 to reinforce the valve 30 as discussed above.

Figure 7:
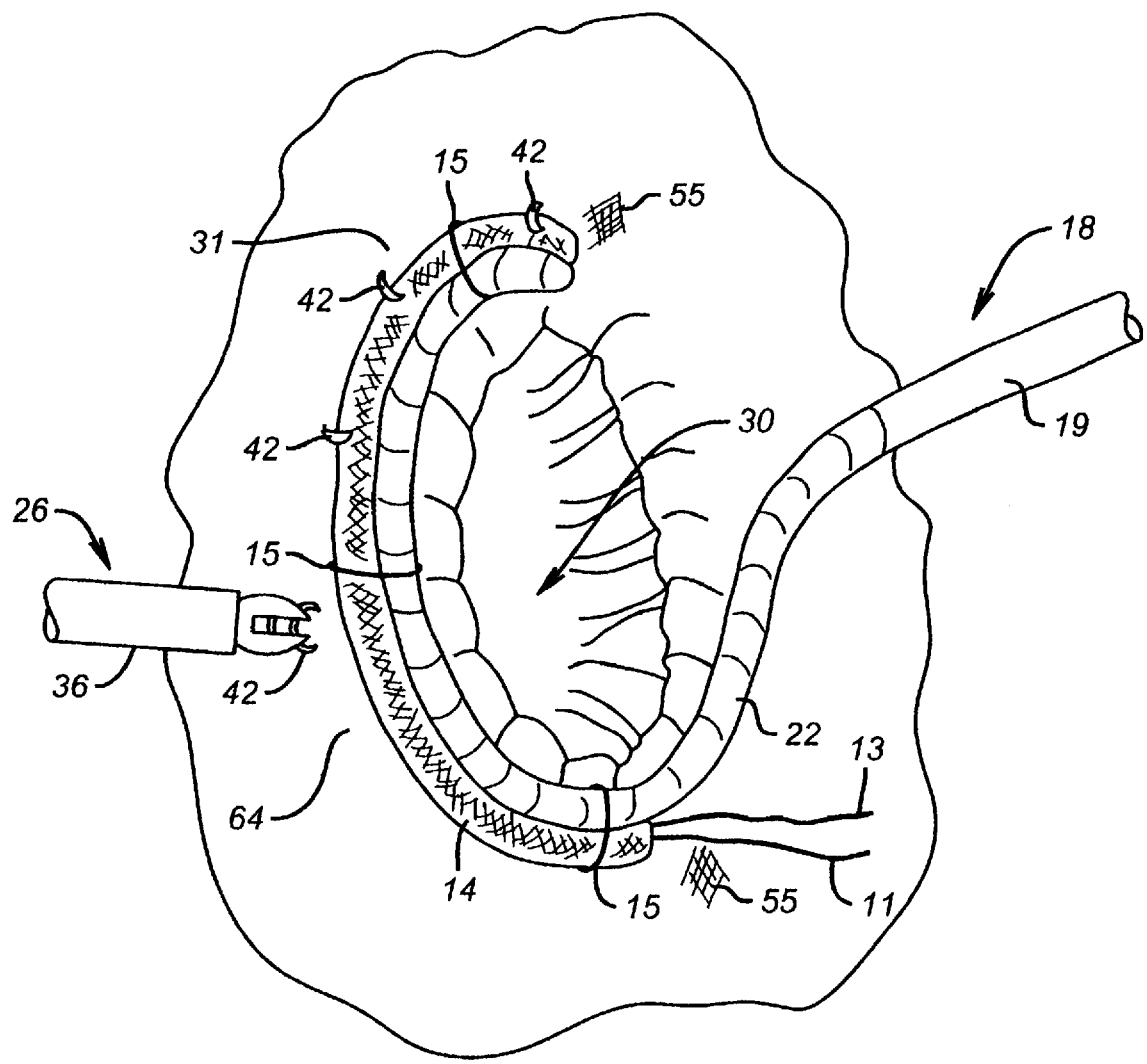
FIG. 7 is a view illustrating an embodiment of an annuloplasty device being positioned and stapled in position in a heart valve.

In FIG. 7, stem 19 and curvature adjustable portion 22 of instrument 18 position band 14 adjacent valve 30. Curvature adjustable portion 22 is adjusted, as described above, to substantially conform the curvature of band 14 to the curvature of valve 30. Band 14 may be temporarily attached to curvature adjustable portion 22 by sutures 15, or the like, which may be removed after stapling. Staple delivery portion 36 of stapling device 26 is positioned to deliver staples or clips 42 for attaching band 14 to tissue 31 adjacent valve 30.

Figure 8:
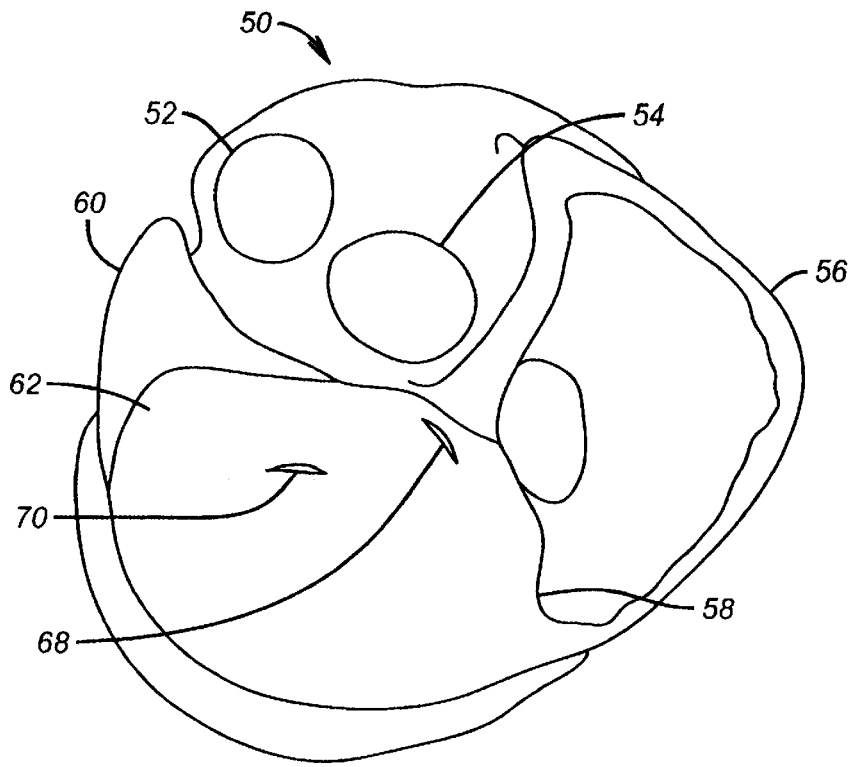
FIG. 8 is a view illustrating a human heart.
Figure 9:
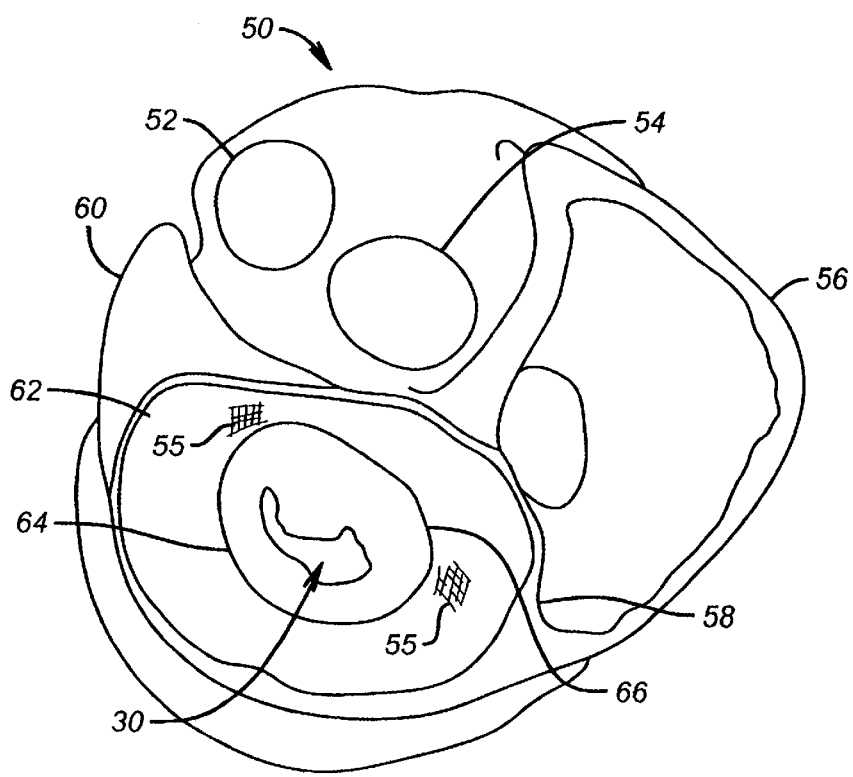
FIG. 9 is a view of the heart as depicted in FIG. 8, having a portion cut away to reveal a mitral valve.

A human heart 50, FIG. 8, also shown with a portion cut away, FIG. 9, includes a pulmonary artery 52, an aorta 54, a right atrium 56, an inter atrial septum 58, a left atrial appendage 60, a left atrium 62, a posterior mitral valve annulus 64 and an anterior mitral valve annulus 66. A pair of incisions 68 and 70 can be made in the left atrium 62. The incision 68 is sized and positioned to permit the instrument 18, FIG. 8, to be inserted to position the band 14 adjacent the posterior mitral valve annulus 64, FIG. 9, of the mitral valve 30. The incision 70 is sized and positioned to permit the stapling device 26 to be inserted and positioned adjacent the valve annulus 66.

As a result, an apparatus for attaching a prosthesis in-situ includes the annuloplasty band 14, the positioning instrument 18 for holding and positioning the band 14 on a heart valve annulus 64, and the stapling device 26 for attaching the band 14 to the annulus 64 simultaneously with the band 14 being held in the annulus 64 by the positioning instrument 18.

Apparatus is provided for attaching a prosthesis in-situ such as a flexible and adjustable annuloplasty band. A positioning instrument is used for holding and positioning the band in a heart valve annulus. The instrument may include a curvature adjustable portion for adjusting the band to the curvature of the heart valve annulus. The curvature adjustable portion is provided at a first end of the instrument and a curvature adjustment actuating means is provided at a second end of the instrument, opposite the first end. If desired, the instrument may include a fixed curvature for positioning the band in the heart valve annulus.

The apparatus provides a new method for attaching a prosthesis in-situ whereby a first and a second incision are made in a native heart. The annuloplasty band, as described above, is provided and is held by the positioning instrument. The positioning instrument is then inserted into the first incision and the annuloplasty band is positioned in engagement with the valve annulus. A stapling instrument is then inserted into the second incision, and the band is stapled to the annulus simultaneously with the band being held in engagement with the annulus by the positioning instrument. Provided that the positioning instrument has an adjustable curvature rather than a fixed curvature, the curvature adjustable portion of the instrument is adjusted so that the band is simultaneously adjusted to fit the curvature of the annulus.

In view of the foregoing, apparatus for attaching a prosthesis in-situ preferably includes a positioning instrument having a curvature adjustable portion at a first end thereof and a curvature adjustment actuating device at a second and opposite end thereof. As an alternative, a positioning instrument having a handle and a fixed curvature at one end may also be used. Either positioning device may be used for holding and positioning an annuloplasty band in a heart valve annulus. An advantage of using the positioning instrument with the curvature adjustable portion is that the instrument can be adjusted to conform to the curvature of the heart valve annulus.

The band is flexible and can be adjusted by the manipulation of two separate adjustment sutures, preferably color coded for adjustment of the front or back half of the anterior mitral or tricuspid valve annulus. The band is a portion of a ring that does not need to be attached on the anterior side of the annulus. The band can be held in position by the positioning instrument and attached to the annulus with staples.

A first incision formed in the left atrium permits the positioning tool to be positioned at the heart valve annulus. A second incision in the left atrium permits the stapler to be positioned at the annulus adjacent the positioning instrument. The stapler can then be used to staple the band to the annulus simultaneously with the band being held at the annulus with the positioning instrument. The band is carried by the curvature adjustable portion of the positioning instrument, or alternatively by the fixed curvature portion of the positioning instrument.

In operation, the embodiments disclose an apparatus and a method for stapling an annuloplasty band in-situ including a flexible and adjustable annuloplasty band attached to a positioning instrument intended to hold the band at a specific location adjacent to the annular tissue for attachment with staples. The positioning fixture could be an instrument like the Genzyme EndoFlex(r) handle that allows changes in the curvature of the fixture by placing tension on an internal wire running down the center of the fixture. A simple curved rod could also be used to position the band for stapling into place. Previous holders have not been designed to facilitate holding the band adjacent to the tissue for stapling. The band could contain two separate adjustment sutures, preferably color-coded for adjustment of the left or right half of the anterior mitral or tricuspid valve annulus. The band would be a portion of a ring, such as a Baxter-Cosgrove(tm) ring that attaches to the posterior portion of the annulus and does not need to be attached on the anterior side of the annulus.

The procedure for a mitral valve would expose the heart so one or two small incisions could be made in the left atrium. The instrument for positioning the prosthesis and the stapler would be inserted through these incisions. The stapler may be an endoscopic stapler with an extended tip that is from about 4 inches to about 15 inches in length. If the operation were being performed without cardiopulmonary bypass (CPB), purse string sutures would be used to prevent leakage around the shaft of the positioning instrument or the shaft of the stapler. The positioning instrument would be used to hold the prosthesis in position against the heart while the stapler was fired to lock the ring onto the annulus. Visualization could be accomplished using fluoroscopy or echocardiography if the heart is beating. If the heart is stopped, visualization can be accomplished with endoscopic instruments or by direct sight. The adjustment sutures would exit the atrium through the fibrous trigones 55, FIGS. 7 and 9, adjacent to the interatrial septum at the point where the aorta and the left atrial wall meet on the base of the heart. The final adjustment of the band can be accomplished after the heart is beating using color flow echocardiography that clearly allows visualization of both the two or three dimensional shape of the annulus and visualization of the regurgitant flow.

As a result, one embodiment provides apparatus for attaching a prosthesis in-situ including an annuloplasty band, a positioning instrument for holding and positioning the band in a heart valve annulus, and a stapling or clip applying device for attaching the band to the annulus simultaneously with the band being held in the annulus by the positioning instrument.

Another embodiment provides a method of attaching a prosthesis in-situ including making a first and a second incision in a native heart. An annuloplasty band is provided along with a positioning instrument for holding and positioning the band in a valve annulus of the native heart. The positioning instrument is inserted into the first incision for positioning the annuloplasty band in engagement with the valve annulus. A stapling or clip applying instrument is inserted into the second incision for stapling or clipping the band to the annulus simultaneously with the band being held in engagement with the annulus by the positioning instrument.

A further embodiment provides apparatus for attaching a prosthesis in-situ including an adjustable annuloplasty band and a positioning instrument for holding and positioning the band in a heart valve annulus. The instrument includes a curvature adjustable portion at a first end for adjusting the band to conform to the heart valve annulus. A second end of the instrument, opposite the first end, includes a curvature adjustment actuating means. A stapling or clip applying device attaches the band to the annulus simultaneously with the band held in the annulus by the positioning instrument.

As it can be seen, the principal advantages of these embodiments are a reduction in time and trauma associated with mitral valve repair by replacing sutures with staples that can be applied more quickly through smaller, less traumatic incisions.

The proposed invention allows rapid placement of an annuloplasty band so the time that a patient is exposed to CPB is greatly reduced or possibly eliminated. This invention will also allow the attachment of an annuloplasty band with a small incision because the tip of a stapler can go through an incision that is much smaller than the incision required for placement of needles into the annular tissue. The invention may allow implantation of an annuloplasty band without the use of CPB and the associated morbidity. The proposed device and procedure may significantly reduce morbidity, particularly if the use of CPB and the morbidity associated with it can be eliminated. If the morbidity associated with the operation can be reduced, then surgical practice will shift toward treating the lesions at an early stage or the disease when the only requirement is reinforcement of the annulus to prevent continued enlargement.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A method for attaching a prosthesis in-situ comprising the steps of:

making a first and a second incision in a native heart;

providing an annuloplasty band;

providing a positioning instrument for holding and positioning the band in a valve annulus of the native heart;

inserting the positioning instrument into the first incision;

positioning the annuloplasty band in engagement with the valve annulus;

inserting a stapling instrument into the second incision; and stapling the band to the annulus simultaneously with the band being held in engagement with the annulus by the positioning instrument.

2. The method as defined in claim 1 further comprising the steps of:

adjusting a portion of the positioning instrument for adjusting the band to fit the annulus.

3. The method as defined in claim 1 wherein the band is flexible.

4. The method as defined in claim 1 wherein the instrument has a fixed curvature for positioning the band at the heart valve annulus.

5. The method as defined in claim 1 wherein the band is adjustable.

6. The method as defined in claim 5 wherein the instrument includes a movable curvature adjustment actuating means at another end thereof, opposite the one end.

7. The method as defined in claim 6 further comprising the step of:

moving the curvature adjustment actuating means for adjusting the band to conform to the heart valve annulus.

8. The method as defined in claim 7 wherein the band is an incomplete ring.

9. The method as defined in claim 4 wherein the instrument has a curvature adjustable portion for adjusting the band to conform to the heart valve annulus.

10. The method as defined in claim 1 wherein the curvature adjustable portion is at one end of the instrument.

* * * * *